United States Patent [19]
Poulsen et al.

[11] 4,367,732
[45] Jan. 11, 1983

[54] SKIN BARRIER

[75] Inventors: Finn Poulsen, Vaerløse; Peter Samuelsen, Rungsted Kyst, both of Denmark

[73] Assignee: Coloplast A/S, Espergaerde, Denmark

[21] Appl. No.: 325,788

[22] Filed: Nov. 30, 1981

[30] Foreign Application Priority Data

Dec. 5, 1980 [DK] Denmark .......................... 5209/80

[51] Int. Cl.³ .............................................. A61L 15/00
[52] U.S. Cl. .................................. 128/156; 128/283
[58] Field of Search .............. 128/155, 156, 283, 295; 428/262; 260/29.1 R, 31.8 N; 3/1

[56] References Cited

U.S. PATENT DOCUMENTS

| | | | |
|---|---|---|---|
| 3,908,658 | 10/1975 | Marsan .................................. | 128/283 |
| 4,204,540 | 5/1980 | Cilento et al. ....................... | 128/283 |
| 4,253,460 | 3/1981 | Chen et al. ........................... | 128/283 |
| 4,296,745 | 10/1981 | Raymond ............................ | 128/283 |

Primary Examiner—Dalton L. Truluck
Assistant Examiner—T. J. Wallen
Attorney, Agent, or Firm—Lawrence Rosen

[57] ABSTRACT

A skin barrier consisting of an elastic film (16), secured to the film a layer (18) of at least weakly elastic adhesive material, these two components together having low resistance to quick deformation and rapid recovery to substantially the original shape after deformation, the plastic properties of the adhesive thereby being compensated by the elasticity of the film. Optionally there may be a releasable protective cover (20,22) on the other side of the adhesive layer. The adhesive material consists of a hydrocolloid, preferably sodium carboxymethylcellulose, dispersed in a continuous phase consisting of a mixture of (a) a physically cross-linked elastomer which is a styrene-olefin-styrene block copolymer, (b) a hydrocarbon resin tackifier which is a polymer or copolymer of cyclopentadiene, dicyclopentadiene or α- or β-pinene, (c) a plasticizer for the elastomer which is compatible at least with the styrene blocks thereof and decreases the upper glass transition temperature thereof, preferably dioctyl adipate, (d) an antioxidant, and (e) optionally an oily extender compatible with the olefin blocks of the elastomer.

10 Claims, 1 Drawing Figure

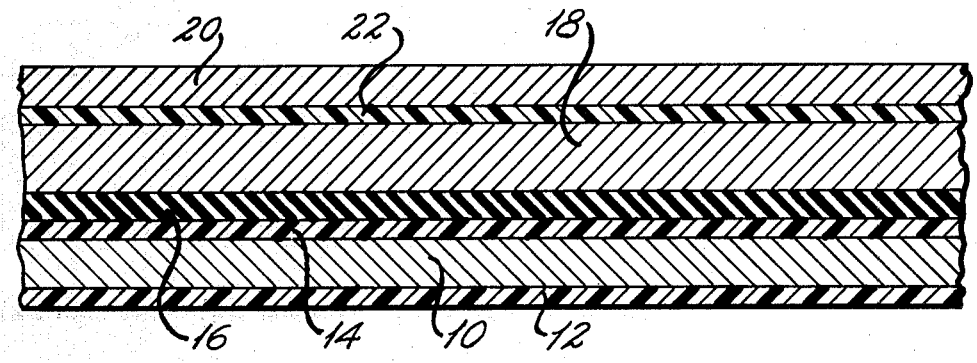

SKIN BARRIER

FIELD OF INVENTION

The present invention relates to a skin barrier consisting of a layer of adhesive, on one side of this a non-adhesive watertight film and on the other side optionally a detachable protective cover.

The skin barrier according to the invention is usable, a.o. for bandaging purposes, especially on movable part of the body such as joints, or on parts of the body having shapes strongly differing from the planar, where it attaches to the curvature of the body surface; moreover for the protection of parts of the skin and for sealing around body openings, especially around protruding body parts such as colostomies, ileostomies and urostomies.

BACKGROUND AND OBJECT OF INVENTION

Various skin barriers and similar materials are known for these and similar purposes, and it is common for them all that they are adhering to the skin. However, they are not all provided with a watertight film. They all suffer from various drawbacks. Thus, from U.S. Pat. No. 3,339,546 there is known a skin barrier, in the specification called a bandage, adapted to adhere to moist surfaces; especially the oral cavity is aimed at. This known bandage consists of a water-impervious film having secured to one surface thereof an adhesive gum-like bonding composition consisting of a blend of a water soluble or swellable hydrocolloid, e.g. polyvinyl alcohol, powdered pectin, gelatin or carboxymethylcellulose, and a water insoluble viscous gum-like elastic binder, e.g. natural rubber, silicone rubber, polyurethane rubber or notably polyisobutylene. The bandage according to U.S. Pat. No. 3,339,546 is unelastic but to some degree plastic, and the bonding composition rather has the nature of a highly viscous fluid whereas the film is described as polyethylene, which is unelastic. The material is hard and needs substantial force to be deformed, it has a very low elongation at break and does not recover to the original shape after deformation. As it is highly viscous, it only partly follows body movements when placed on movable parts, and if it is used for sealing around ostomies there is a risk of leakage. When using a bandage like this for very curved body parts, e.g. a heel, it is recommended to cut a number of incisions in the edge of a round bandage to enable it to follow the curvatuve of the part of the body; without the incisions the bandage would pucker or go to pieces if one seeks to deform it. The hydrocolloid in the bandage just described ensures that it can adhere to and retain contact with moist, e.g. sweaty surfaces. To improve adhesion and give desired consistency there can optionally be a mineral oil or vaseline present; the viscous gum-like binder gives dry tack and coherence.

From U.S. Pat. No. 3,908,658 there is known a closure and sealing composition for ostomies, also suitable for adhering ostomy-draining pouches to the skin, said composition being water-insoluble and essentially composed of a pressure sensitive adhesion gel body having a uniform surface and internal properties of tack, cohesive strength providing elasticity, flexibility, and compressibility and manual kneadability, said gel consisting essentially of a mixture of mineral oil, styrene-isobutylene copolymer and ethylene-vinyl acetate copolymer. The composition does not typically contain hydrocolloids, but hydrophilic substances such as pregelled starch may be present. This composition has similar drawbacks as the bonding composition according to U.S. Pat. No. 3,339,546, yet has a bigger elongation at break.

To remedy these drawbacks, in British Pat. No. 1,576,522, corresponding to U.S. Pat. No. 4,231,369, there has been proposed a sealing material for ostomy systems having low resistance to quick deformation and rapid recovery to the original shape after deformation, and which consists of a shaped, gel-like blend of a hydrocolloid dispersed in a continuous phase consisting of a physically cross-linked elastomer, viz, a styrene-olefin-styrene block copolymer (or possibly an ethylene-propylene block copolymer) and a hydrocarbon tackifier and optionally also an oil extender and an antioxidant.

This sealing material, which may also be used as skin barrier for other purposes, is splendidly elastic and flexible (whereby is meant bendable out of the plane), it adheres well to the skin and follows its movements and also movements of joints well only the movements are not too big. Because of the hydrocolloid the material absorbs secretions. However, adhesion defects may occur at big movements, e.g. when the material is used as or in bandages at joints. Especially such adhesion defects may occur where the material is used as skin barrier provided with a watertight film on the side turned away from the skin because normal films for the purpose are flexible but unelastic. Adhesion defects may also occur if the material absorbs much moisture, notably if the absorption is irregular. An irregular absorption of moisture may for instance occur at the use as skin barrier over suppurating wounds where the wound itself will yield much liquid, the immediate surroundings less, viz, only sweat. Irregular absorption of moisture may for instance also take place at the use of the material as sealing gasket around stomies, where the parts adjacent the ostomy absorbs liquid from the intestinal discharges and the parts a little more distant only absorb sweat.

By liquid absorption in the known material it causes the material to expand substantially uniformly in all three dimentions (longitudinal and transversal direction, thickness) and this causes a tendency of the material to pucker and let the adhesive contact with the skin go in the areas where the moisture absorption is highest. When using it around ostomies there will occur puckers in the adhesive or sealing material just around the ostomy opening which may give rise to serious skin discomforts because the often very agressive (enzyme-containing) intestinal liquors thereby come into contact with the skin. Also at even supply of moisture the known sealing material just described has a tendency to partly let the skin go and form folds and puckers, especially at its use as bandage on joints because of its three-dimensional expansion combined with the normal unelastic properties of the cover film. The adhesion to the skin is weaker than the forces causing the three-dimensional expansion.

It has now surprisingly been found that the particular drawback of three-dimensional expansion and consequent puckering can be met by the combined measure of reducing the elasticity of the sealing or adhesive material disclosed in U.S. Pat. No. 4,231,369 and bonding that material to an elastic film. It has also been surprisingly found that this reduction of the elasticity of the adhesive material can be achieved by the aid of a plasticizer for the styrene-olefin-styrene block copolymer constituting the elastomer of the said material or at least for the hard styrene blocks thereof. When a material so plasticized or softened absorbs moisture, it will be able to "flow" internally, which means that the forces causing the three-dimensional expansion become weaker because the internal flow may convert the three-dimensional expansion into a largely uni-directional expansion provided that other circumstances favour this; and precisely this is favoured by the bonding of the adhesive material to the elastic film.

In this connection it should be mentioned that U.S. Pat. No. 2,703,573 discloses, i.a., a self-adhering bandage relatively non-adherent to human skin, comprising a strip of fabric coated with an emulsion of styrene latex and a tackifier, said tackifier consisting essentially of an emulsion of polystyrene or a copolymer of styrene and a solvent plasticizer or, e.g., polyethylene glycol di-2-ethyl hexoate; alternatively, the emulsion may be an emulsion of the styrene latex and an emulsified solvent plasticizer, e.g. dioctyl adipate. It is noteworthy that this prior art product is relatively non-adherent to the skin, in contradistinction to the present material, which must be adherent to the skin. As the known material is relatively non-adherent, the problem of losing contact with the skin locally, and puckering, does not exist. Should it exist, it could not be solved by the provisions of the patent; the reason is that the substance plasticized according to the patent is a styrene latex, i.e. a homogeneous material, especially in dried condition when it is no longer a latex, except for variations in the molecular weight (degree of polymerization). The tackifier or plasticizer has the express purpose of retaining self-cohesion at drying, i.e. to enable the emulsified particles of the styrene latex to unite so as to form a coherent mass is relatively non-adherent and free from stickiness.

In connection with the present invention, however, the purpose of the plasticizer is to soften a heterogenous material, the styrene-olefin-styrene block copolymer the blocks of which are mutually incompatible, so that the adhesive material can "flow" internally.

In case there is used a styrene copolymer according to the disclosure of U.S. Pat. No. 2,703,573, it is part of the tackifier and plasticizer emulsion and not a part of the component being plasticized. Apart from this, it is not disclosed what the styrene may be copolymerized with in order to form the copolymer.

BRIEF DISCLOSURE OF INVENTION

In accordance with the invention, the skin barrier essentially consists of the following elements in combination:
(A) a non-adhesive, substantially water-impervious, elastic film, secured to one of the faces of an adhesive layer of
(B) an adhesive material which is a gel-like, at least weakly elastic mixture consisting of
 (I) a continuous phase consisting of
  (a) at least one physically cross-linked elastomer selected from the group consisting of styrene-olefin-styrene block copolymers,
  (b) at least one hydrocarbon tackifier resin selected from the group consisting of polymers and copolymers of cyclopentadiene, dicyclopentadiene, α-pinene and β-pinene,
  (c) a polar plasticizer for the elastomer, being compatible at least with its styrene blocks and decreasing the upper glass transition temperature of the styrene blocks of the elastomer,
  (d) an antioxidant, and
  (e) 0–25%, based on the weight of the adhesive material, of an oily extender,
 (II) dispersed in the continuous phase (I) a discontinuous phase consisting of at least one hydrocolloid which is swellable in water, and
(C) optionally a dethachable protective cover secured to the other face of the adhesive layer,
the aggregate of said water-impervious elastic film (A) and the adhesive material (B) adhering thereto, but without the optional protective layer (C), having a low resistance to quick deformation and after deformation a rapid recovery to substantially its original shape.

BRIEF DESCRIPTION OF DRAWING

The drawing in large scale schematically shows a longitudinal section of a piece of the skin barrier according to the invention. The claimed skin barrier consists of an elastic film 16 (element (A) above) secured to a layer 18 of elastic material as described above (as element B), the latter optionally secured to a protective cover consisting of paper 20 coated with silicone wax 22.

Elements 10, 12 and 14 are not a part of the skin barrier but serve purposes in connection with its manufacture; they are described later.

The drawing does not necessariy show the correct relative thicknesses of the several layers.

DETAILED DESCRIPTION OF INVENTION

The adhesive layer is deformable under the influence of weak and rapidly acting forces, thus having a low elasticity modulus and a large elongation. It has a very low flowing when dry and not exposed to outer forces. With the expression that the elastomer must be physically cross-linked is meant that the cross links in the polymer of which it consists is not of a chemical (covalent) nature but of a physical nature which means that there are areas or domains within the elastomer which have a high crystallinity, i.e. a high glass transition temperature. Precisely this property of the material known from U.S. Pat. No. 4,231,369 causes that when absorbing moisture it expands largely uniformly in all three dimensions. It has surprisingly been found that a limited plastification of the physical cross-links in the elastomer with the plasticizer mentioned under (c), which must be compatible with the styrene domains of the elastomer, causes that absorption of moisture in the adhesive material in use precominantly expresses itself as an increase in dimension in the thickness direction and only very small expansion in the two other dimensions. Thereby the puckering of the adhesive material, discussed hereinabove, is avoided even at high moisture absorption, and hence also that the adhesion gets lost in parts of the adhesive material. Especially it is obtained that sealing problems when using the material for ostomy adhesive and sealing gaskets are avoided. The lesser elasticity and higher plasticity of the material caused by the plasticizer, which may give a tendency to some degree of permanent change of shape or "set" after deformation is counteracted thereby that the watertight film is elastic, whereby the combination adhesive layer-film has the desired properties with respect to a low elasticity modulus and a small or no permanent change of shape or "set" after deformation.

Because of this the skin barrier according to the invention is not only suited as sealing and adhesive gasket for ostomy pouches and other ostomy closure means, but also for bandaging purposes where skin, mucous membranes or wounds are to be protected against the immediate surroundings such as intestinal, wound or glandular secretions or again bacterial attack, the action of the air, evaporation, light, impact and pressure. If the skin barrier is to be used in connection with real bandages change of these may take place without disturbing the surface of the skin or wound since the skin barrier is retained on the skin at the change, and moreover it will in itself limit bandage changes to a minimum. The material is skin and wound friendly and because of the elastic properties it may in many cases draw edges of wounds together and render superfluous the use of clips, which may give a less visible wound healing than would otherwise be the case. By use around movable parts of the body, e.g. joints, or on soft parts of the body, which for instance are apt to form folds, the mobility is preserved and the skin barrier follows the movements. The skin barrier seals well around protruding part of the body, e.g. ostomies.

As elastomer there is used as mentioned styrene-olefin-styrene block copolymers. They are A-B-A block copolymers having polystyrene end blocks which are thermodynamically incompatible with the polyolefin rubber middle blocks. Consequently there is phase separation in the solid state. The polystyrene constitutes about a third of the molecule and hard polystyrene domains are therefore a kind of discontinuous phase distributed in a rubber matrix. The hard areas constitute the physical cross-links which bind the ends of the molecules together to a network reminding of that formed by a conventional vulcanized rubber (caoutchouc). Since the high cohesive strength of the block copolymer originates from the physical cross-links (instead of from the chemical cross-links as in vulcanized materials) it is easy to work. In comparison with conventional rubbers the styrene-olefin-styrene block copolymers have low molecular weights, of the A-blocks around 2000–100,000 and of the B-blocks around 25,000–200,000. The content of styrene units is normally below 40%. These block copolymers have two glass transition temperatures, one below, the other considerably above room temperature.

The aliphatic blocks may be based on isoprene, butadiene, other short chain alkadienes or alkenes such as mixtures of ethylene and butylene, or polyisobutylene. It has been found according to the invention that the elastomer particularly advantageously is a styrene-isoprene-styrene block copolymer. Very suitable is the material sold under the registered trade mark "Cariflex" Tr-1107, which contains about 28% by weight styrene units.

As softener for the two types of blocks of the elastomer, or at least for the hard styrene blocks a plasticizer must be present. The plasticizer especially has to decrease the higher of the glass transition temperatures. As this plasticizer in principle may be used a series of substances having polar nature to a substantial degree, thus for instance naphthenic oils, which however should be avoided because they may be cancerogenic and/or allergenic.

The best suitable are esters of di- and polybasic organic acids which have been fully esterified with aliphatic monovalent alcohols, especially those having 6–12 carbon atoms, and esters of polyethylene and polypropylene glycols with carboxylic acids, for the above reason preferably aliphatic acids. Particularly suitable are dioctyl adipate and dioctyl pthalate and of these dioctyl adipate is preferred according to the invention, firstly because it has been found to give to the invention, firstly because it has been found to give the best results with respect to a moderate decrease of the elasticity of the elastomer, and secondly as a consequense of a general tendency to prefer aliphatic to aromatic compounds for materials for use on the human body. For the same reasons esters of the said acids with phenols are avoided.

The tackifier resin is necessary to give the needful adhesion to the skin and is an integral component of the continuous phase.

The antioxidant is necessary to maintain the properties of the elastomer; some commercial elastomers of the type concerned incidentally contain antioxidant from the factory. The type of antioxidant is not critical and ordinary reference books will give examples. Suitable antioxidants are butylated hydroxy toluenes such as methylene-bis-(4-methyl-6-t-butylphenol) or 1-hydroxy-2,6-di-t-butyl-4-methylbenzene.

Apart from the above described plasticizer there may be an oily extender present. It is substantially incompatible with the styrene domains of the elastomer but compatible with the soft olefin moiety. As oily extender there may especially be used paraffinic oils or vaseline. If desired vegetable oils may be used but since they have a somewhat polar nature they may also act on the styrene domains and thereby increase the effect of the plasticizer to a degree not fully clear; they are therefore preferably avoided.

The discontinuous phase consists of the hydrocolloid. Its purpose first and foremost is to ensure the adhesion of the skin barrier to skin and mucous membranes even when they are moist. It is well-known that conventional plasters lose the grip and adherence to the skin when exposed to moisture.

The hydrocolloid must be capable of swelling rapidly under the influence of water, and of transporting water rapidly. It should preferably also be soluble in water. Suitable hydrocolloids are carboxymethyl celluloses and carboxymethyl starches and alkali metal derivatives thereof, polyvinyl alcohol, gelatin, powdered pectin, vegetable gums such as gum guar, gum arabic, locust bean gum, karaya, high molecular weight polyethylene or polypropylene glycols, polyoxymethylene and similar polymers. According to the invention sodium carboxymethylcellulose is preferred; also a blend of sodium carboxymethylcellulose and gum guar in the proportion about 36:16 by weight is suitable.

In the continuous phase or as a further dispersed phase additives having various skin-friendly and/or therapeutic purposes may be present. Such additives may for instance be pH controlling systems such as sodium, potassium or magnesium citrates, or bacteriocidal, bacterostatic, fungicidal or fungistatic agents and special proteins which might contribute to a fast wound healing, e.g. collagen.

As mentioned it is important that the watertight film is elastic. Comparatively few plastic foil materials are elastic but suitable films for the purpose consist of polyurethane, styrene-isoprene copolymers, styrene-butadiene block copolymers, butadiene rubbers, isoprene rubbers, neoprene rubbers, silicone rubbers, butyl rubbers, chloroprene rubbers or mixtures thereof. According to the invention it is particularly preferred that the water-tight elastic film is a polyurethane film.

The proportions of the several components may vary within rather wide limits. The amount of the elastomer, however, is normally somewhat higher than in the material known from U.S. Pat. No. 4,231,369 and according to the invention constitutes 10–40% by weight of the adhesive layer, preferably 20–40%. According to the invention the composition of the adhesive layer expressed in % by weight may be: elastomer 10–40%, preferably 20–40%; tackifier resin 15–45%, preferably 30–40%; plasticizer for the two domains of the elastomer as defined 2–12%, preferably 8–12%; antioxidant 0.5–2.5%; oily extender 0–25% and hydrocolloid 10–55%, preferably 20–40%.

An especially preferred composition is about 25% styrene-isoprene block copolymer (notably one containing about 20% styrene unites, "Cariflex" ® TR 1107), about 35% tackifier resin, about 9% dioctyl adipate, about 1% antioxidant and about 30% sodium carboxymethylcellulose.

For special purposes the adhesive layer in the skin barrier may have a high thickness, e.g. up to 6 mm or more, but according to the invention the thickness is normally 0.25–3 mm, preferably about 1.1 mm, and the thickness of the elastic watertight film normally according to the invention 10–15μ, preferably about 30μ.

In practice the skin barrier is prepared by pouring the adhesive material in molten condition on the film, after which there is rolled to the desired thickness of the adhesive layer. If desired the adhesive material may be rolled onto the film in a non-molten state, but softened by heat. During the application of the adhesive layer the film must be supported on a suitable material because the film will absorb plasticizer from the adhesive material and swell; because of physical forces (e.g. van der Waal's forces) the swelling only takes place in the thickness dimension when the film is fixed to the backing, but otherwise may take place in all directions and involve puckering. When the adhesive layer is cold the connection between the same and the film will remain smooth, even if the film has swelled. Some films when supplied by the manufacturer are supported on a suitable material and a particularly suitable material is paper coated with polyethylene on the side facing the adhesive material and on the other side with a silicone wax. This support material may remain on the skin barrier as a protective cover which is only removed when it is to be taken into use.

The adhesive material may be prepared in a manner similar to that described in U.S. Pat. No. 4,231,369. Preferably the physically cross-linked styrene-olefin-styrene elastomeric copolymer is mixed with the antioxidant (if not present from the factory of the copolymer), the hydrocarbon resin tackifier, the plasticizer and optionally the oily extender, after which the blend is heated at a suitable temperature, normally within the range of 80°–170° C. When the desired temperature has been reached and the blend is homogenuous, optionally by agitation, the hydrocolloid is added at the same temperature and the mixture stirred until the hydrocolloid has been evenly dispersed in the mixture of the other components. Thereafter the mass is cooled for later used, or directly used for pouring onto the supported fiom as described above.

EXAMPLE

A skin barrier having the structure schematically shown in the drawing was prepared in the following manner A web of paper 10 which on the underside 12 had silicone wax and on the top side was coated with a thin film 14 of polyethylene, and above that an elastic film 16 of polyurethane having a thickness of about 28μ, was coated with a melt of adhesive material having the following composition: 25.1% "Cariflex" ® TR 1107, 35.1% "Arkon" ® P 90 (a hydrogenated polycyclopentadiene adhesive from Arkawa Forest Chemical Industries Ltd.), 8.8% dioctyl adipate, 30% sodium carboxymethylcellulose and 1.0% antioxidant, viz, methylene-bis-(4-methyl-6-t-butylphenol). After partial solidification the melt was rolled to a thickness of 1.1 mm whereby the adhesive material constituted a layer 18. After cooling the whole was wound to a roll of the web. The paper with polyethylene layer and silicone wax layer is an extra protective cover to be removed when the skin barrier, consequently consisting of the layers 16 and 18, is taken into use.

On top of the adhesive layer a protective cover may be placed, consisting of a paper web 20 coated on the side facing the adhesive layer with a layer of silicone was 22.

When the skin barrier is taken into use, pieces of desired shape and size are cut out.

We claim:

1. A skin barrier, essentially consisting of the following elements in combination:
    (A) a non-adhesive, substantially water-impervious, elastic film, secured to one of the faces of an adhesive layer of
    (B) an adhesive material which is a gel-like, at least weakly elastic mixture consisting of
        (I) a continuous phase consisting of
            (a) at least one physically cross-linked elastomer selected from the group consisting of styrene-olefin-styrene block copolymers,
            (b) at least one hydrocarbon tackifier resin selected from the group consisting of polymers and copolymers of cyclopentadiene, dicyclopentadiene, α-pinene and β-pinene,
            (c) a polar plasticizer for the elastomer, being compatible at least with its styrene blocks and decreasing the upper glass transition temperature of the styrene blocks of the elastomer,
            (d) an antioxidant, and
            (e) 0–25%, based on the weight of the adhesive material, of an oily extender,
        (II) dispersed in the continuous phase (I) a discontinuous phase consisting of at least one hydrocolloid which is swellable in water,
the aggregate of said water-impervious elastic film (A) and the adhesive material (B) adhering thereto having a low resistance to quick deformation and after deformation a rapid recovery to substantially its original shape.

2. The skin barrier claimed in claim 1, wherein the water-impervious elastic film (A) is a polyurethane film.

3. The skin barrier claimed in claim 1, wherein the elastomer (a) is a styrene-isoprene-styrene block copolymer.

4. The skin barrier claimed in claim 1, wherein the plasticizer (c) compatible both with the styrene and olefin domains of the elastomer (a) and is selected from the group consisting of esters of polyethylene glycol and polypropylene glycol with aliphatic carboxylic acids and esters of di- or polybasic carboxylic acids with aliphatic alcohols.

5. A skin barrier as claimed in claim 4, wherein the plasticizer is dioctyl adipate.

6. A skin barrier as claimed in claim 1, wherein the hydrocolloid (II) dispersed in the contiguous phase (I) is sodium carboxymethylcellulose.

7. The skin barrier claimed in claim 1, wherein the gel-like, at least weakly elastic mixture constituting the elastic layer (B) has the following composition, the percentages all being based on the weight of the material:
 (I) 45-90% continuous phase consisting of
  (a) 10-40% physically cross-linked elastomer,
  (b) 15-45% hydrocarbon tackifier resin,
  (c) 2-12% polar plasticizer for the elastomer,
  (d) 0.5-2.5% antioxidant,
  (e) 0-25% oily extender, and
 (II) 10-55% hydrocolloid as discontinuous phase.

8. The skin barrier claimed in claim 7, wherein the gel-like, at least weakly elastic mixture has the following composition, based on the total weight of the material:
 (I) about 70% continuous phase consisting of
  (a) about 25% styrene-isoprene-styrene block copolymer containing about 28% (based on the copolymer weight) styrene units as elastomer,
  (b) about 35% tackifier resin,
  (c) about 9% dioctyl adipate as plasticizer for the elastomer,
  (d) about 1% antioxidant, and
 (II) about 30% sodium carboxymethylcellulose as dispersed hydrocolloid.

9. The skin barrier claimed in claim 1, wherein the layer of adhesive has a thickness of 0.25-3 mm and the elastic film a thickness of 10-50μ.

10. A skin barrier, essentially consisting of the following elements in combination:
 (A) a non-adhesive, substantially water-impervious, elastic film, secured to one of the faces of an adhesive layer of
 (B) an adhesive material which is a gel-like, at least weakly elastic mixture consisting of
  (I) a continuous phase consisting of
   (a) at least one physically cross-linked elastomer selected from the group consisting of styrene-olefin-styrene block copolymers,
   (b) at least one hydrocarbon tackifier resin selected from the group consisting of polymers and copolymers of cyclopentadiene, dicyclopentadiene, α-pinene and β-pinene,
   (c) a polar plasticizer for the elastomer, being copatible at least with its styrene blocks and decreasing the upper glass transition temperature of the styrene blocks of the elastomer,
   (d) an antioxidant, and
   (e) 0-25%, based on the weight of the adhesive material, of an oily extender,
  (II) dispersed in the continuous phase a discontinuous phase consisting of at least one hydrocolloid which is swellable in water,
 (C) a detectable protective cover secured to the other face of the adhesive layer,
the aggregate of said water-impervious elastic film (A) and the adhesive material (B) adhering thereto, but without the protective layer (C), having a low resistance to quick deformation and after deformation a rapid recovery to substantially its original shape.

* * * * *